(12) United States Patent
Fukutani (10) Patent No.: US 9,615,751 B2
(45) Date of Patent: Apr. 11, 2017

(54) OBJECT INFORMATION ACQUIRING APPARATUS AND OBJECT INFORMATION ACQUIRING METHOD

(75) Inventor: Kazuhiko Fukutani, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 485 days.

(21) Appl. No.: 14/007,386

(22) PCT Filed: Apr. 9, 2012

(86) PCT No.: PCT/JP2012/002465
§ 371 (c)(1),
(2), (4) Date: Sep. 25, 2013

(87) PCT Pub. No.: WO2012/140865
PCT Pub. Date: Oct. 18, 2012

(65) Prior Publication Data
US 2014/0018659 A1    Jan. 16, 2014

(30) Foreign Application Priority Data
Apr. 12, 2011  (JP) .................... 2011-088312

(51) Int. Cl.
*A61B 5/00* (2006.01)
*A61B 8/00* (2006.01)
*G01N 21/17* (2006.01)

(52) U.S. Cl.
CPC .......... *A61B 5/0095* (2013.01); *A61B 5/7203* (2013.01); *A61B 8/429* (2013.01);
(Continued)

(58) Field of Classification Search
CPC combination set(s) only.
See application file for complete search history.

(56) References Cited

U.S. PATENT DOCUMENTS 6,216,540 B1  4/2001 Nelson et al. .................. 73/633
8,260,403 B2  9/2012 Fukutani et al. ............. 600/476
(Continued)

FOREIGN PATENT DOCUMENTS

JP   A 2010-167001   8/2010
JP   A 2010-537700   12/2010
WO  WO 2010/009747   1/2010

OTHER PUBLICATIONS

M. Xu et al., "Photoacoustic Imaging in Biomedicine", *Review of Scientific Instruments*, vol. 77, 044101 (Apr. 17, 2006).
(Continued)

*Primary Examiner* — Katherine Fernandez
*Assistant Examiner* — Farshad Negarestan
(74) *Attorney, Agent, or Firm* — Fitzpatrick, Cella, Harper & Scinto (57) ABSTRACT

An object information acquiring apparatus, comprising: a plurality of detecting elements which detect an acoustic wave generated from an object irradiated with light and convert the acoustic wave into detection signals; a signal determining unit which determines a detection signal detected by a detecting element which is not in acoustic contact with the object, of the plurality of detecting elements; a signal acquisition unit which generates a corrected detection signal by deleting at least a region which is not based on an acoustic wave generated from the interior of the object, from the determined detection signal; and an image processor which forms image data of the object from a detection signal detected by a detecting element which is in acoustic contact with the object and from the corrected detection signal.

16 Claims, 5 Drawing Sheets

(52) U.S. Cl.
CPC ....... *A61B 8/4281* (2013.01); *G01N 21/1702* (2013.01); *G01N 2021/1706* (2013.01)

(56) References Cited

U.S. PATENT DOCUMENTS

| | | | |
|---|---|---|---|
| 2004/0039379 A1 | 2/2004 | Viator et al. | 606/9 |
| 2010/0087733 A1 | 4/2010 | Nakajima et al. | 600/437 |
| 2010/0191109 A1 | 7/2010 | Fukutani et al. | 600/437 |
| 2011/0046484 A1 | 2/2011 | Adams | 600/440 |
| 2011/0128816 A1 | 6/2011 | Baba et al. | 367/11 |
| 2011/0232385 A1* | 9/2011 | Nanaumi | A61B 5/0095 73/602 |
| 2011/0245667 A1 | 10/2011 | Tokita | 600/437 |
| 2012/0130222 A1 | 5/2012 | Kobayashi et al. | 600/407 |
| 2012/0183190 A1 | 7/2012 | Fukutani et al. | 382/128 |
| 2012/0243369 A1 | 9/2012 | Sudo et al. | 367/13 |
| 2012/0296192 A1 | 11/2012 | Fukutani | 600/407 |
| 2013/0245420 A1 | 9/2013 | Fukutani | 600/407 |
| 2014/0058245 A1 | 2/2014 | Oishi et al. | 600/407 |

OTHER PUBLICATIONS

T. de Beer et al., "Laser-Based Non-Fluorescence Detection Techniques for Liquid Separation Systems", *Journal of Chromatography A*, Elsevier Science Publishers B.V., NL, vol. 971, No. 1-2, pp. 1-35 (2002).

\* cited by examiner

OBJECT INFORMATION ACQUIRING APPARATUS AND OBJECT INFORMATION ACQUIRING METHOD

TECHNICAL FIELD

The present invention relates to an object information acquiring apparatus and an object information acquiring method.

BACKGROUND ART

In the medical field, active progress has been made in research of optical imaging technology that forms an image of information from the interior of a living organism, which is obtained on the basis of incident light when light is irradiated onto the living organism from a light source such as a laser. One optical imaging technology of this kind is Photoacoustic Tomography (PAT). In photoacoustic tomography, pulsed light generated from a light source is irradiated onto a living organism, an acoustic wave is generated from the living tissue which has absorbed the energy of the pulsed light that has propagated or diffused inside the organism, and this acoustic wave (typically, an ultrasonic wave) is detected. In other words, using the difference in absorptivity of the light energy in an examination site, such as a tumor, and other tissue, the elastic wave generated when the examination site momentarily expands upon absorbing irradiated light energy is received with an acoustic probe (also called a probe or transducer). By analyzing this detection signal, it is possible to obtain an image which is directly proportional to the initial pressure distribution or the light absorption energy density distribution (the product of the absorption coefficient distribution and the light amount distribution) (NPL 1).

Furthermore, by performing measurement using light of various wavelengths, this image information can be used for quantitative measurement of specific properties of the organism, such as the total hemoglobin density or blood oxygen saturation, or the like. In recent years, photoacoustic tomography of this kind has been use to make active progress in preclinical research for creating images of blood vessels in small animals, and clinical research which applies this principle to the diagnosis of breast cancer, prostate cancer, carotid artery plaque, and so on.

CITATION LIST

Non Patent Literature

[NPL 1]
"Photoacoustic imaging in biomedicine", M. Xu, L. V. Wang, REVIEW OF SCIENTIFIC INSTRUMENT, 77, 041101, 2006

SUMMARY OF INVENTION

Technical Problem

In photoacoustic tomography, if the object under examination is not in acoustic contact with a portion of the detection surface of the acoustic probe, then the received data obtained by the detecting elements of the acoustic probe in that region may include a signal other than the acoustic wave generated inside the organism. In cases where a signal of this kind is received, if an image is reconstructed by using all of the detection signals obtained, then a false image (artifact) is generated apart from the initial sound pressure distribution or absorbed light energy density distribution inside the object, and hence there has been a problem in that the image is markedly degraded.

The present invention was devised in view of problems of this kind. It is an object of the present invention to provide technology for reducing image deterioration even in cases where an object is not in acoustic contact with the detecting elements of the acoustic probe.

Solution to Problem

The present invention provides an object information acquiring apparatus, comprising:

a plurality of detecting elements which detect an acoustic wave generated from an object irradiated with light and convert the acoustic wave into detection signals;

a signal determining unit which determines, from the detection signals, a detection signal detected by a detecting element which is not in acoustic contact with the object, of the plurality of detecting elements;

a signal acquisition unit which generates a corrected detection signal by deleting at least a region which is not based on an acoustic wave generated from an interior of the object, from the detection signal detected by the detecting element which is not in acoustic contact with the object; and an image processor which forms image data of the object from a detection signal detected by a detecting element which is in acoustic contact with the object and from the corrected detection signal.

The present invention also provides an object information acquiring method comprising:

a step in which a plurality of detecting elements detect an acoustic wave generated from an object irradiated with light and convert the acoustic wave into detection signals;

a step in which a signal determining unit determines, from the detection signals, a detection signal detected by a detecting element which is not acoustic contact with the object, of the plurality of detecting elements;

a step in which a signal acquisition unit generates a corrected detection signal by deleting at least a region which is not based on an acoustic wave generated from an interior of the object, from the detection signal detected by the detecting element which is not in acoustic contact with the object; and a step in which an image processor forms image data of the object from a detection signal detected by a detecting element which is in acoustic contact with the object and from the corrected detection signal.

Advantageous Effects of Invention

According to the present invention, it is possible to provide technology for reducing image deterioration even in cases where an object is not in acoustic contact with the detecting elements of an acoustic probe.

Further features of the present invention will become apparent from the following description of exemplary embodiments with reference to the attached drawings.

DESCRIPTION OF EMBODIMENTS

Below, the present invention is described in more details with reference to the drawings. Constituent elements which are the same are in principle labeled with the same reference numerals and description thereof is omitted here.

(Photoacoustic Image-Forming Apparatus)

Figure 1:
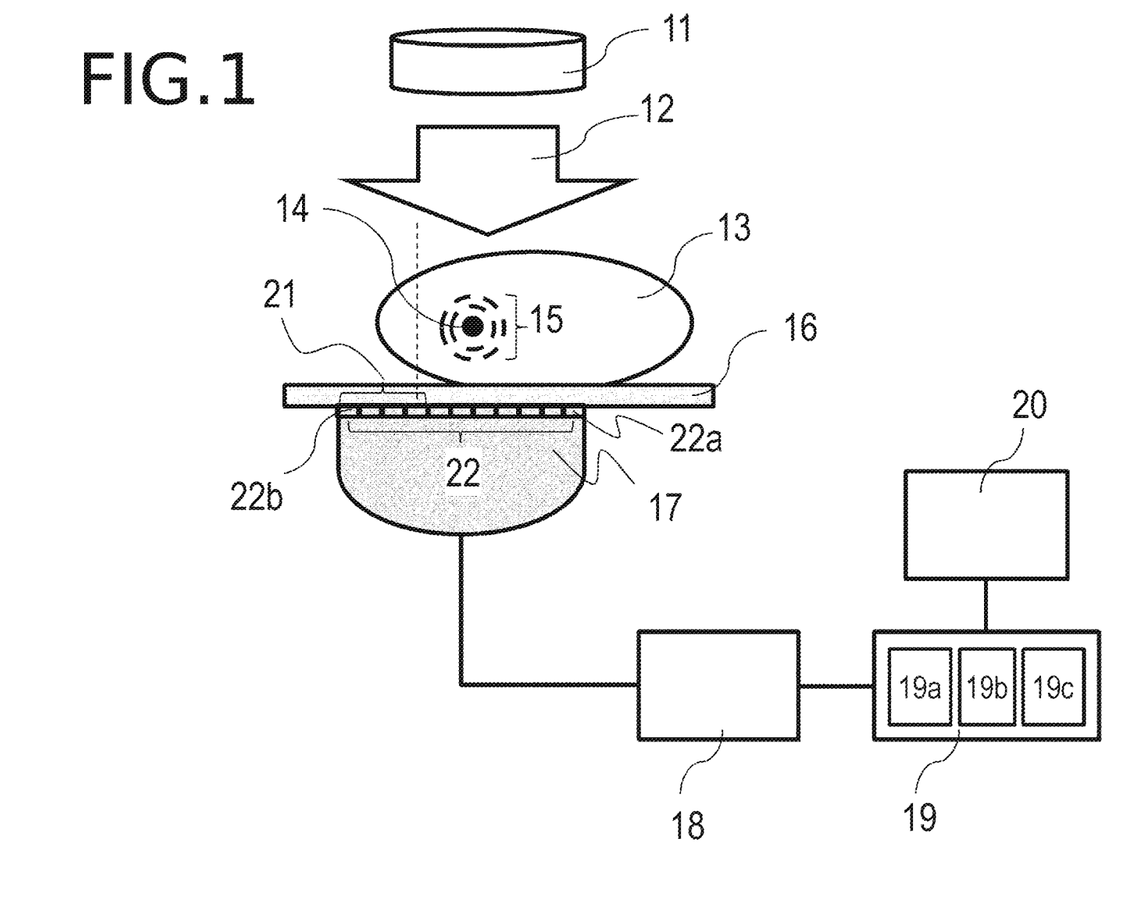
FIG. 1 is a diagram showing a schematic view of the composition of a photoacoustic image-forming apparatus according to the present invention.

The composition of a photoacoustic image-forming apparatus relating to the present embodiment is described here with reference to FIG. 1. The photoacoustic image-forming apparatus relating to the present embodiment is an apparatus which creates an image of optical characteristics value information from the interior of an object. The optical characteristics value information generally means the initial sound pressure distribution, the absorbed light energy density distribution, or an absorption coefficient distribution derived from these. As described hereinafter, the optical characteristics value information is also called object information, and therefore the photoacoustic image-forming apparatus according to the present invention may also be understood as an object information acquiring apparatus.

The photoacoustic image-forming apparatus according to the present embodiment comprises, as basic hardware, a light source 11, an acoustic probe 17 forming an acoustic detector, and a signal processing unit 19. Pulsed light 12 emitted from the light source 11 is obtained by processing the light to a desired shape by an optical system (not illustrated) such as a lens, mirror, optical fiber, diffusion plate, or the like, and is irradiated onto the object 13, such as a living organism. When one portion of the light energy which has propagated inside the object 13 is absorbed by a light absorbing body, such as a blood vessel (which consequently forms a sound source) 14, an acoustic wave (and typically an ultrasonic wave) 15 is generated due to thermal expansion of the light absorbing body 14. This is also called a "photoacoustic wave". The acoustic wave 15 is detected by detecting elements 22 of the acoustic wave probe 17, amplified and converted to digital by a signal acquisition system 18, and then converted to image data of the object by a signal processor 19. Moreover, the image data is displayed as an image on the display apparatus 20.

(Light Source 11)

If the object is a living organism, light having a specific wavelength which is absorbed by a particular component, of the components which constitute the living organism, is irradiated from the light source 11. The light source may be provided in an integrated fashion with the image-forming apparatus of the present embodiment, or may be provided separately from the image-forming apparatus. For the light source, it is desirable to use a pulsed light source capable of generating a pulsed light of the order of several nanoseconds to several hundred nanoseconds. More specifically, in order to generate a photoacoustic wave efficiently, a pulse width of approximately 10 nanoseconds is used.

For the light source, it is desirable to employ a laser since a large output can be obtained, but it is also possible to use a light-emitting diode, or the like, instead of a laser. As a laser, it is possible to use lasers of various types, such as a solid-state laser, a gas laser, a dye laser, a semiconductor laser, or the like. The irradiation timing, light intensity, and the like, are controlled by a light source control unit, which is not illustrated. The light source control unit is generally integrated with the light source. In the present invention, the wavelength of the light source used is desirably a wavelength at which the light propagates to the interior of the object. More specifically, if the object is a living organism, then the wavelength of the light is no less than 500 nm and no more than 1200 nm.

(Object 13 and Light Absorbing Body 14)

These elements do not constitute a portion of the photoacoustic image-forming apparatus of the present invention, but are described below. The main purpose of the photoacoustic image-forming apparatus according to the present invention is for contrast imaging of blood vessels, diagnosis of malign tumors or vascular disease in humans and animals, follow-up observation of chemotherapy, and the like. Therefore, it is envisaged that the object 13 is a living organism, and more specifically, a diagnostic site in a human or animal, such as a breast, finger, foot, or the like. In the case of small animals such as mice, the whole of animal is the object rather than a particular site.

The light absorbing body 14 inside the object indicates an object having a relatively high absorption coefficient inside the object. Although it depends on the wavelength of the light used, if a human being is the measurement object, then the light absorbing body 14 may correspond to oxygenated or deoxygenated hemoglobin, or blood vessels containing a large amount of these, or a malign tumor which includes a large number of new blood vessels. In the present invention, "object information" refers to the acoustic wave generating source distribution which is produced by irradiation of light, and this means the initial sound pressure distribution inside the organism or an absorbed light energy density distribution or absorption coefficient distribution derived from these. Moreover, "object information" means the density distribution of the substances which constitute the living tissue (and in particular, the oxygenated and reduced hemoglobin). For example, the density distribution of the substance is the oxygen saturation, or the like. The object information which is formed into an image is called "image data".

(Holding Plate 16)

A contact surface on the object 13 is flattened by the holding plate 16 in order to couple the object acoustically with the detecting elements 22 of the acoustic wave probe 17 over a broad range. Normally, the holding plate 16 is used in order to hold the object 13 or to maintain same in a uniform shape. In order to receive the acoustic wave efficiently, it is desirable to choose a material for the holding plate which is close to the acoustic impedance of the object. If the object is a breast, for example, then desirably, a plate formed in polymethyl pentene is desirable. The shape of the plate is desirably a flat plate, but it is possible to use any shape which enables close contact between the acoustic wave receiver and the plate installation surface. If the plate is a flat plate, then the thinner the plate thickness, the better, from the viewpoint of attenuation of the acoustic wave, and so on, but the plate should desirably have a thickness which prevents deformation of the shape of the plate. Typically, the plate has a thickness of approximately 5 mm to 10 mm. The holding plate 16 can be omitted in the present invention, provided that it is possible to impart a function similar to that of the holding plate to the detection surface of the acoustic wave probe.

(Acoustic Wave Probe 17)

The acoustic wave probe 17 is a detector which detects a photoacoustic wave generated at the surface of an object and the interior of an object, and the like, due to pulsed light, and the acoustic wave probe 17 detects an acoustic wave and then converts the wave to an analog electrical signal. Hereinafter, the acoustic wave probe 17 is also referred to simply as a probe or a transducer. It is possible to use an acoustic wave probe of any kind, such as a transducer based on a piezoelectric effect, a transducer based on light resonance, or a transducer based on change in capacitance, or the like, provided that the probe is capable of detecting an acoustic wave signal. In the acoustic wave probe 17 according to the present embodiment, typically, a plurality of detecting elements 22 are arranged one-dimensionally or two-dimensionally. By using a multi-dimensional arrangement of elements in this way, it is possible to detect an acoustic wave in a plurality of locations, simultaneously, and the measurement time can be shortened. As a result of this, it is possible to reduce the effects of vibration of the object, and the like.

(Signal Acquisition System 18)

Desirably, the photoacoustic image-forming apparatus according to the present embodiment has a signal acquisition system 18 which amplifies an electrical signal obtained from an acoustic wave probe 17 and converts the electrical signal from an analog signal to a digital signal. The signal acquisition system 18 is typically constituted by an amplifier, an A/D converter, a FPGA (Field Programmable Gate Array) chip, and the like. Desirably, if a plurality of detection signals are obtained from the acoustic wave probe 17, then the signal acquisition system 18 is able to process this plurality of signals simultaneously. By this means, it is possible to shorten the time taken to form an image. In the present specification, the "detection signal" is a concept which also includes a digital signal obtained by AD conversion from an analog signal acquired from the acoustic wave probe 17. The detection signal may also be called a "photoacoustic signal".

(Signal Processing Unit 19)

The main role of the signal processing unit 19 is to process a digital signal obtained from a signal acquisition system 18, and to then perform image reconstruction to create an image of the optical characteristics value information from the inside of the object. Furthermore, the signal processing unit 19 according to the present invention detects, and reduces or deletes, unwanted acoustic wave signals received by detecting elements in a region 21 which is not in acoustic contact with the object, in the digital signals obtained from the signal acquisition system 18, this process being a characteristic feature of the present invention. As a result of this, it is possible to reduce image degradation caused by unwanted acoustic signals of this kind.

There now follows a description of the region 21 which is not in acoustic contact with the object referred to here. More specifically, the region 21 is a region where the object 13 and the detection surface of the probe do not lie in physical contact, via the holding plate 16 or another acoustic wave transmission material, such as gel, on a vertical line drawn from the center of the detection surface of the detecting element 22 of the acoustic wave probe 17, as shown in FIG. 1. In other words, this means a region where a medium which does not readily transmit an acoustic wave, such as air, is interposed on the vertical line drawn through the object 13 and the detecting element 22. In FIG. 1, a detecting element which is not in acoustic contact with the object is taken as a detecting element 22b, and a detecting element which is in acoustic contact with the object is taken as a detecting element 22a.

Normally, a computer such as a work station is typically used for the signal processing unit 19, and the detection signal processing and image reconstruction processing, and the like, are carried out by previously programmed software. The software used in a work station includes, for example, a signal determining module 19a, a signal processing module 19b and an image reconstructing module 19c.

The signal determining module 19a determines a detecting element 21a which is in a region that is not in acoustic contact with the object, on the basis of the received signal. The signal processing module 19b generates a corrected detection signal by correcting the signal received by a detecting element that has been determined as a detecting element 21a in a region 21 which is not in acoustic contact with the object. The image reconstructing module 19c carries out image reconstruction using this corrected signal.

Here, the signal determining module 19a, the signal processing module 19b and the image reconstructing module 19c are normally handled as a computer, such as a workstation and associated software, and therefore are often treated as a single signal processing apparatus 19, as shown in FIG. 1. In the present invention, the signal determining module corresponds to a signal determining unit, the signal processing module corresponds to a signal acquisition unit and the image reconstructing module corresponds to an image processing unit.

The basic function of the signal determining module 19a and the signal processing module 19b is to determine the detecting elements 22b which are in a region that is not in acoustic contact with the object, from the digital signal obtained by the signal acquisition system 18. Correction processing, such as unwanted signal reduction processing, and the like, of the data received by the detecting elements thus determined, is then carried out. The details of this processing method are described hereinafter. The basic function of the image reconstructing module 19c is to form image data based on image reconstruction, by using corrected detection signal data obtained from the signal processing module 19b. The image reconstruction algorithm used is, for example, back projection in a time domain or Fourier domain, as commonly used in tomography technology. If a large amount of time is available for reconstruction, then it is possible to use an image reconstruction method such as an iterative method, which uses repeated processing. Various methods can be employed as an image reconstruction technique in PAT, as described in NPL 1. Typical image reconstruction methods are a Fourier transform method, universal back projection method, deconvolution method, filtered back projection method, an iterative reconstruction method, and so on. In the present invention, it is possible to use an image reconstruction technique of any kind.

(Display Apparatus 20)

The display apparatus 20 is an apparatus which displays image data output by a signal processing unit 19 and typically, a liquid crystal display, or the like, is employed. The display apparatus may also be provided separately from the photoacoustic image-forming device according to the present invention.

(Detection Signal Processing)

Figure 2:
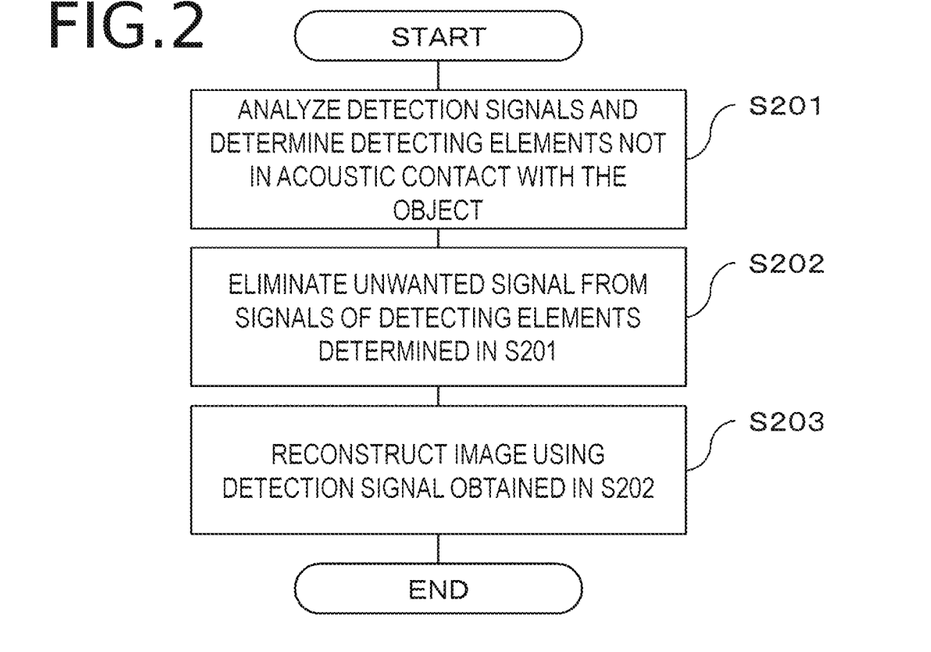
FIG. 2 is a flow diagram illustrating an example of processing of a detection signal according to the present invention.

Next, one example of a correction processing method for unwanted signals in the detection signals, which is performed by the signal processing unit 19 and which is a characteristic feature of the present invention, will be described with reference to FIG. 2 and FIG. 3. The step numbers given below coincide with the step numbers in FIG. 2.

Step (1) (Step S201): A step of analyzing the detection signals and determining detecting elements which are not in acoustic contact with the object.

For example, in the signal determining module 19a, detecting elements which are not in a stat of acoustic contact with the object are determined by using the characteristics of the signals received from detecting elements 22b which are not in acoustic contact with the object. FIG. 3A is one example of a signal which is received by a detecting element 22b that is not in acoustic contact with the object, and FIG. 3B is one example of a signal which is received by a detecting element 22a which is in acoustic contact with the object. The horizontal axis in the drawings represents a sample number, and in the case of 20 MHz sampling, one measurement is performed every 50 nanoseconds. The vertical axis represents the intensity of the received acoustic wave. In other words, in the case of 20 MHz sampling, the horizontal axis shows the sampling time when the sample number is multiplied by 50 nanoseconds. In the case of normal photoacoustic imaging, the timing of light irradiation is taken to be zero seconds.

Figure 3A:
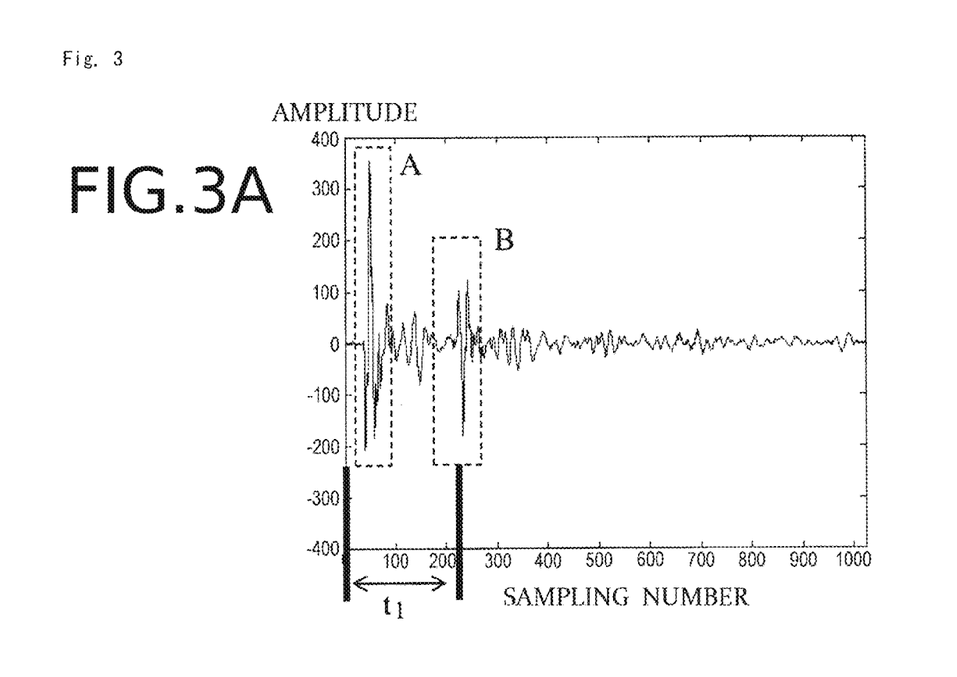
FIGS. 3A and 3B are schematic drawings showing examples of a detection signal from a detecting element.
Figure 3B:
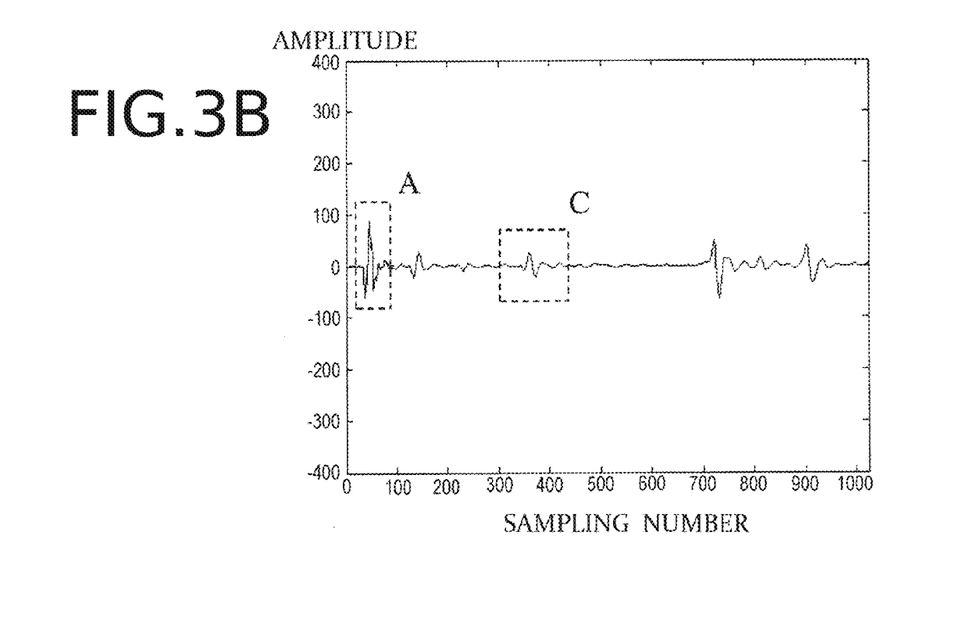

Comparing FIGS. 3A and 3B, the signal indicated by the dotted line B in FIG. 3A is not detected in FIG. 3B. This signal is received when a photoacoustic wave generated at the surface of the acoustic wave probe (a signal in the region indicated by the dotted line A) is fully reflected at the interface between the holding plate 16 and the air, and is received again as an acoustic wave. In other words, this is a signal which is received as a large signal, if the detecting element is a detecting element 22b which is not in acoustic contact with the object. Since the signal is reflected at the interface with the air, then a characteristic feature of the signal is that the phase is reversed (the waveform is reversed) with respect to a signal in the region indicated by the dotted line A.

Furthermore, if the thickness of the holding plate 16 and the speed of sound therein are known, then it is possible to predict, in advance, that the signal will be detected at a specific timing, for instance, at t1 in FIG. 3A. A signal in the region indicated by dotted line C in FIG. 3B is not measured in FIG. 3A, and is therefore inferred to be produced by a photoacoustic wave generated inside the object.

Next, a method of determining a detecting element 22b which is not in acoustic contact with the object will be described.

A signal in the region indicated by the dotted line A in FIG. 3A is a detection signal (photoacoustic signal) which is generated due to light being irradiated directly onto the surface of the probe. This signal may be observed in FIG. 3B, but a comparison of FIGS. 3A and 3B shows that the intensity in FIG. 3A is clearly greater. For example, if the detecting element is in acoustic contact with the object, then the surface of the detecting element covers the object, and therefore the pulsed light does not reach the surface of the detecting element directly. For instance, supposing that a photoacoustic wave is generated by diffused light, or the like, then only a small signal is observed.

On the other hand, if the detecting element is not in acoustic contact with the object, then when light is irradiated onto the object from the opposite side to the probe, as shown in FIG. 1, the light is irradiated directly onto the surface of the detecting element, and a large signal is observed from the surface of the detecting element. More specifically, a detecting element which is not in acoustic contact with the object can be determined by comparing the intensity of this signal. More specifically, a detecting element showing an intensity equal to or greater than a predetermined threshold value is determined as a detecting element which is not in acoustic contact with the object. The predetermined threshold value referred to here is a value which is determined experimentally, for example, one half of the peak value of the detection signal (photoacoustic signal) generated by irradiating light directly onto the surface of the acoustic wave probe when no object is present. Furthermore, since this threshold value is an intrinsic value of the apparatus, then desirably the threshold value is adjusted respectively for each apparatus. The timing at which the predetermined threshold value is specified may be immediately before the actual measurement or the threshold value may be specified in advance, for each type of apparatus. The predetermined threshold value thus specified can be used at any time by storing the value in a memory (memory unit), for example.

Furthermore, it is possible to envisage the following method as an alternative method. The waveforms indicated by the dotted line A and the dotted line B in FIG. 3A are characteristic of a signal which is received by a detecting element 22b which is not in acoustic contact with the object. Therefore, these two signals are used as a template to obtain a correlation with the whole detection signal. By means of this correlation, it is possible to determine a signal which is received by a detecting element that is not in physical contact with the object and a signal which is received by a detecting element that is in acoustic contact with the object. In this case, the portion indicated by the dotted line A is a detection signal based on a first acoustic wave. More specifically, a detecting element showing a correlation equal to or greater than a predetermined threshold value is determined as a detecting element 22b which is not in acoustic contact with the object. The predetermined threshold value referred to here is 0.2, for instance, if the correlation value is 1 when the signal is completely matching. However, since this threshold value is an intrinsic value of the apparatus, then desirably the threshold value is adjusted respectively for each apparatus. The timing at which the these threshold values are specified may be immediately before the actual measurement or the values may be specified in advance, for each type of apparatus. The predetermined threshold value thus specified can be used at any time by storing the value in a memory (memory unit), for example.

The determination method described here is no more than one example. The essence of the present invention is to extract and determine the characteristics of a signal which is received by a detecting element that is not in acoustic contact with the object, and any method may be employed provided that it does not depart from the scope of this essence.

Process (2) (step S202): A step of eliminating unwanted signals from the signals of the detecting elements determined in S201.

For example, in the signal processing module 19b, a new detection signal group is created by deleting the whole of a signal which has been received by a detecting element 22b determined as not in acoustic contact with the object. Alternatively, a corrected signal is generated by reducing to zero a signal received by a detecting element 22b which is determined as not in acoustic contact with the object. In general, when a detecting element 22 is not in acoustic contact with the object, it is not able to receive a photoacoustic wave generated inside the object. Consequently, all of the data received in a region which does not make acoustic contact with the object does not contribute to the image produced when creating an image of the initial pressure distribution or light energy density distribution inside the object. Therefore, it is possible to set all of the data to zero, or to delete the detection signal itself and assume that the detecting element is not present. In other words, in the present step, a signal which is separate to the digital signal obtained from the signal acquisition system 18, in other words, a corrected digital signal, is generated by carrying out processing such as that described above.

Process (3) (Step S203): A step of carrying out image reconstruction by using the detection signal obtained in S202.

For example, image reconstruction is carried out by using a corrected digital signal which is obtained in S202, whereby an image relating to the initial pressure distribution or the light energy density distribution of the object 15 is formed. In respect of this processing, it is possible to use an image reconstruction process of any kind which is normally employed in photoacoustic tomography. For instance, a method of back projection in a time domain or a field domain, or the like, is employed.

By carrying out the steps described above, in cases where a portion of the detecting elements 22 are not in acoustic contact with the object 13 as in the example in FIG. 1, it is possible to eliminate signals which are not necessary for the formation of an image of the interior of the object. As a result of this, it is possible to provide a photoacoustic image-forming apparatus which shows little image deterioration.

First Embodiment

One example of a photoacoustic image-forming apparatus which employs photoacoustic tomography applying the present embodiment will now be described. This image-forming apparatus is described here with reference to the schematic drawing in FIG. 1. In the present embodiment, a Q-switch YAG laser which generates pulsed light of approximately 10 nanoseconds at a wavelength of 1064 nm was used as the light source 11. The energy of the light pulse emitted from the pulsed light 12 was 0.6 J, and the pulsed light was broadened to a radius of approximately 2 cm using an optical system such as a mirror and a beam expander, or the like. Subsequently, the optical system was set up so as to be able to irradiate the pulsed light onto the object on the opposite side to the acoustic wave probe 17.

Figure 4A:
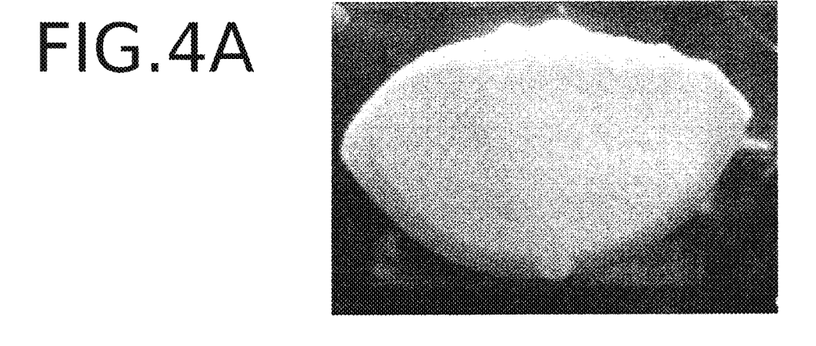
FIGS. 4A to 4C are diagrams showing a measurement object and images obtained by measurement.

A phantom which simulates a breast shape was used as the object 13. The breast-shaped phantom was prepared using urethane rubber, titanium oxide and ink, in such a manner that the reduced scattering coefficient and the absorption coefficient were substantially the same as a breast. Three round bar-shaped cysts having a diameter of 2 mm were buried in the phantom as light absorbing bodies 14. Furthermore, the breast-shaped phantom had a curved surface shape. Therefore, in order to flatten the shape and achieve acoustic coupling with the acoustic wave probe 17, a holding plate 16 formed for 10 mm-thick polymethyl pentene was installed between the acoustic wave probe 17 and the breast-shaped phantom 13. FIG. 4A shows a photograph of the breast-shaped phantom taken from the side of the polymethyl pentene in this case. As FIG. 4A reveals, the breast-shaped phantom does not make close contact in the whole of the region of the polymethyl pentene. In this region, air is interposed between the phantom and the detecting elements, and therefore the phantom and the detecting elements cannot be coupled acoustically. As a result of this, the signal from the detecting elements in this region where close contact is not made is a cause of image degradation.

Furthermore, pulsed light 12 was irradiated onto the breast-shaped phantom which had been set up in this way, on the surface of the phantom opposite to the acoustic wave probe 17, as shown in FIG. 1. The acoustic wave probe 17 employed a 2D array type probe formed of a plurality of detecting elements 22 arranged in a two-dimensional configuration. Furthermore, a portion of the region measured by the 2D array type acoustic wave probe 17 included a region 21 not in acoustic contact with the breast-shaped phantom, as shown in FIG. 1.

Next, the generated photoacoustic wave was received by the plurality of detecting elements 22 of the 2D array type acoustic wave probe 17. The detection signals of these elements were obtained as a digital signal of photoacoustic signal by using a signal acquisition system 18 comprising an amplifier, an A/D converter and an FPGA. Thereupon, the obtained digital signal was transferred to a work station (WS) forming a signal processor 19, and was saved in the WS. Thereupon, the digital signal was analyzed by the signal determining module 19a and the signal processing module 19b, which are software programs inside the WS.

In the present embodiment, signal determination was carried out by using the reception intensity of the photoacoustic wave generated at the surface of the detecting elements. The determination method was as follows. More specifically, in the received acoustic wave signal, the maximum value of the photoacoustic wave generated at the detecting element surfaces as observed during an initial measurement period indicated by the region A in FIG. 3 is detected. If this maximum value is greater than a certain value, then it is taken to be a signal received from a detecting element 22b which is not in acoustic contact with the breast-shaped phantom. The signal in this region is sufficiently large in comparison with noise, and therefore the signal can be determined in a stable fashion. In the present embodiment, if the intensity of the signal was 200 or above, then the signal was judged to be one from a detecting element 22b which was not in acoustic contact with the breast-shaped phantom, and if the intensity was less than 200, then the signal was judged to be from a detecting element 22a which was in acoustic contact with the breast-shaped phantom. Furthermore, a corrected signal was formed in which signals received by detecting elements 22b not in acoustic contact with the breast-shaped phantom were all set to zero.

Figure 4B:
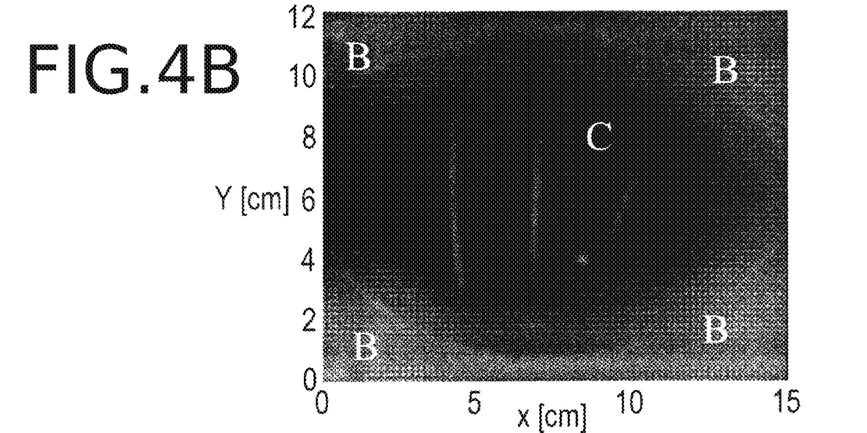
Figure 4C:
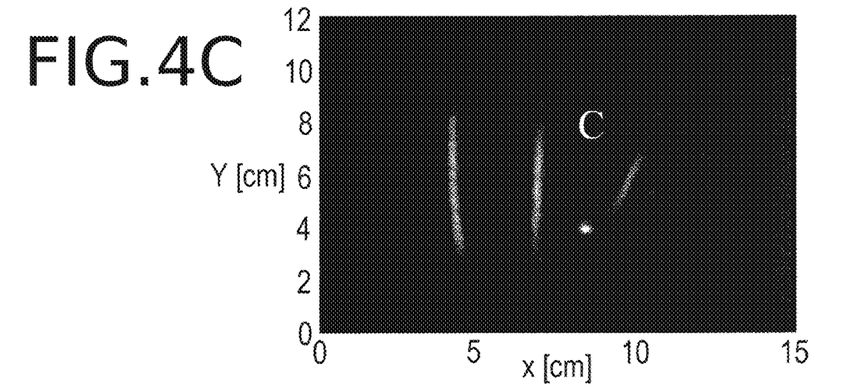

Thereupon, image reconstruction was carried out in the reconstruction module 19c, which is a software program in the WS, using the corrected signal created in this way. Here, three-dimensional volume data was created by using a universal back projection method, which is a time domain method, from among the plurality of image reconstruction techniques. FIG. 4C shows one example of an image obtained in this case. FIG. 4C shows a MIP (Maximum Intensity Projection) image obtained by projecting the maximum brightness in the direction in which all of the absorbing bodies can be imaged, in the three-dimensional image data. Thereupon, an image was calculated by the image reconstruction technique employed as described above, using an uncorrected digital signal which had been saved in the WS. FIG. 4B shows one example of an image obtained in this case. FIG. 4B is an MIP image in which the maximum brightness in the direction where all of the absorbing bodies can be imaged is projected from the three-dimensional image data.

FIGS. 4B and 4C will now be compared. In a signal which is received from a detecting element that is not in acoustic contact with the breast-shaped phantom, a reflected wave of the photoacoustic wave generated at the surface of the probe is observed as shown by the dotted line B in FIG. 3A, and therefore the image produced by this signal appears as the region B in FIG. 4B. The region of the dotted line B in FIG. 3 is an artifact which is present horizontally at a certain depth, and this is caused by a reflected wave of the photoacoustic wave which is generated at the surface of the probe as described above. On the other hand, in FIG. 4C, the unnecessary signal of this kind is deleted, and therefore an image C caused by the photoacoustic wave generated inside the phantom, such as that indicated by the dotted line C in FIG. 3B, appears only. When measuring body tissue, such as a breast, it is not possible to distinguish between an image produced by an acoustic wave generated inside the breast and other images, and therefore an unnecessary image A of this kind can lead to misdiagnosis. In other words, the image in FIG. 4C can be regarded as superior in terms of a diagnostic image.

From the foregoing, by eliminating signals which are not necessary for image formation, from the detection signals of detecting elements that are not in acoustic contact with the object, it is possible to provide a photoacoustic image-forming apparatus capable of generating an image with little degradation which is superior as a diagnostic image to the prior art.

Second Embodiment

Figure 5:
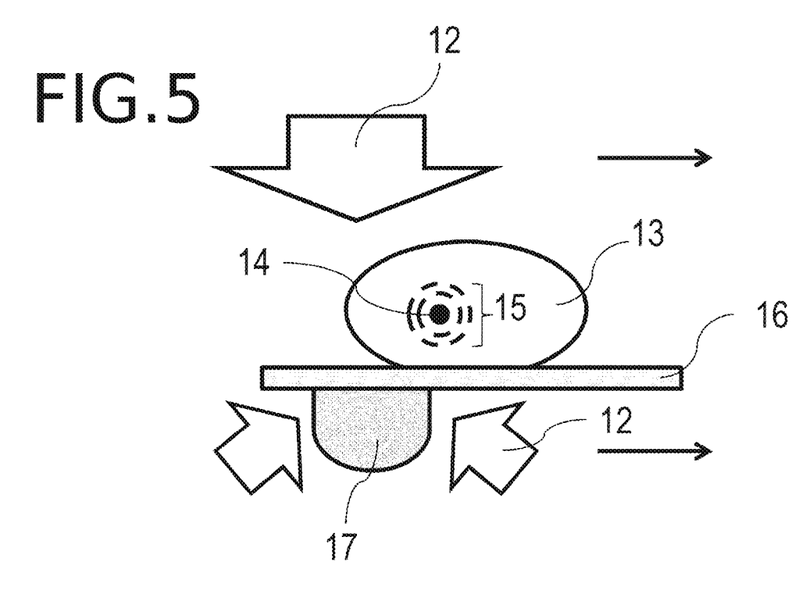
FIG. 5 is a diagram showing a schematic view of the composition of a photoacoustic image-forming apparatus according to the present invention.

One example of a photoacoustic image-forming apparatus which employs photoacoustic tomography applying the present embodiment will now be described with reference to FIG. 5. In the present embodiment, a phantom and a measurement system substantially the same as those of the first embodiment were used. However, in contrast to the schematic drawing of the apparatus in FIG. 1, here, the light 12 was irradiated in the direction of the breast-shaped phantom from the side of the acoustic wave probe 17, as shown in FIG. 5. Furthermore, a scanning action of the acoustic wave probe 17 and the light 12 was performed in order to form an image of the whole of the breast-shaped phantom.

In an apparatus of this kind, in the present embodiment, similarly to the first embodiment, after acquiring a digital signal of the generated photoacoustic wave, the obtained digital signal was transferred to a workstation (WS) forming a signal processor 19 and was saved in the WS. Thereupon, the digital signal was analyzed by the signal determining module 19a and the signal processing module 19b, which are software programs inside the WS.

In the present embodiment, the method of determining the detecting elements 22b which were not in acoustic contact with the object employed a method such as that described below. When pulsed light 12 is irradiated from the side of the acoustic wave probe, then a photoacoustic wave is generated due to the light irradiated onto the probe surface, similarly to the first embodiment. Furthermore, since the photoacoustic wave is fully reflected at the interface between the holding plate 16 and the air, then a photo-acoustic wave having a reversed phase is received again. Since the difference in the reception times of these two acoustic waves is uniform, as indicated by the relationship between the regions A and B in FIG. 3A, and since their shapes are also unique, then it is possible to determine these waves by using this shape.

The specific determination method employed will now be described. Firstly, in a composition where there is no phantom, the signal received when light is irradiated directly onto the surface of the probe is measured, and the photoacoustic wave generated at the surface of the probe and the signal which is received again when this acoustic wave is reflected at the holding plate are extracted from the measured signal. The extracted signal is saved as a template in the workstation (WS) which forms the signal processor 19. Thereupon, the correlations between this template and all of the received signals are calculated, and a detection signal having a high correlation value is determined to be a signal received by a detecting element which is not making physical contact with the object. Furthermore, the detection signals from the detector which are determined in this way are not treated as detection signals, and a new corrected signal which excludes these signals is created.

Thereupon, image reconstruction was carried out in the reconstruction module 19c, which is a software program in the WS, using the corrected signal created in this way. Here, in contrast to the first embodiment, three-dimensional volume data was created by using a Fourier domain. The image of the breast-shaped phantom obtained by a method of this kind was similar to that in FIG. 4C, and a clearer image than FIG. 4B, which is an image acquired by conventional technology, was obtained.

From the foregoing, it is possible to determine detecting elements which are not in acoustic contact with the object, by determining the shape of the detection signal, and it is possible to provide a photoacoustic image-forming apparatus having little image degradation, by eliminating signals which are not necessary for image formation, from the detection signal.

Third Embodiment

One example of a photoacoustic image-forming apparatus which employs photoacoustic tomography applying the present embodiment will now be described. In the present embodiment, the same phantom and measurement system as the first embodiment were used, with the exception that the holding plate 16 was not present. Firstly, similarly to the first embodiment, after acquiring a digital signal of a photoacoustic wave generated by irradiation of pulsed light 12, the obtained digital signal was transferred to a workstation (WS) forming a signal processor 19 and saved in the WS. Thereupon, the digital signal was analyzed in the signal determination and signal processing modules which are software programs in the WS. In the present embodiment, detecting elements which were not in acoustic contact with the phantom were determined by using the reception intensity of the photoacoustic wave generated at the surface of the probe, similarly to the first embodiment. Thereupon, all of the data from the detecting elements determined as not in acoustic contact with the phantom was deleted, and image reconstruction was carried out using only the detection signals from detecting elements which were in acoustic contact with the phantom. The image obtained by a method of this kind was similar to that in FIG. 4C, and a clearer image than FIG. 4B, which is an image obtained by conventional technology, was obtained.

From the foregoing, even if there is no holding plate, by analyzing the intensity of the detection signal, it is possible to determine detecting elements which are not in acoustic contact with the object and by eliminating the detection signals of these elements, it is possible to provide a photoacoustic image-forming apparatus which has little image degradation.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-88312, filed on Apr. 12, 2011, which is hereby incorporated by reference herein in its entirety.

The invention claimed is:

1. An object information acquiring apparatus for an object not in complete acoustic contact with a detection surface, comprising:
    an acoustic probe comprising the detection surface, wherein the acoustic probe is configured to detect an acoustic wave generated from the object irradiated with light at a plurality of detecting elements of the detection surface and convert the acoustic wave detected at each of the plurality of detecting elements into respective analog time-series signals;
    signal acquisition circuitry configured to convert the respective analog time-series signals into respective digital signals;
    a signal processing unit configured to
        receive the digital signals;
        determine, from the received digital signals, an unwanted digital signal corresponding to an analog time-series signal having a signal portion whose waveform is reversed relative to a waveform of another signal portion in the analog time-series signal corresponding to the acoustic wave generated from the object, wherein said unwanted digital signal corresponds to at least one detecting element which is not in acoustic contact with the object;
        generate corrected digital signals by reducing, from the received digital signals, the determined unwanted digital signal; and
        generate object information using the corrected digital signals; and
    an image processor which forms image data of the object from the object information.

2. The object information acquiring apparatus according to claim 1, further comprising a memory unit which stores a predetermined template signal having a signal portion whose waveform is reversed relative to a waveform of another signal portion in the predetermined template signal,
    wherein the unwanted digital signal is a signal whose correlation value with the predetermined template signal is equal to or greater than a threshold value.

3. The object information acquiring apparatus according to claim 2, wherein said signal processing unit is configured to adjust the threshold value.

4. The object information acquiring apparatus according to claim 2, further comprising a holding unit configured to hold the object,
    wherein said memory unit stores the predetermined template signal created based on a signal generated corresponding to an acoustic wave reflected by said holding unit.

5. The object information acquiring apparatus according to claim 2, further comprising a holding unit configured to hold the object,
    wherein said signal processing unit is configured to generate the corrected digital signals by reducing, from the received digital signals outputted at a timing determined based on a thickness of the holding unit and sound velocity in the holding unit, the unwanted digital signal.

6. The object information acquiring apparatus according to claim 1, further comprising a holding unit configured to hold the object.

7. The object information acquiring apparatus according to claim 1, further comprising a holding unit configured to hold the object,
    wherein said signal processing unit is configured to generate the corrected digital signals by reducing, from the received digital signals outputted at a timing determined based on a thickness of said holding unit and sound velocity in the holding unit, the unwanted digital signal.

8. An object information acquiring apparatus for an object not in complete acoustic contact with a detection surface, comprising:
    a plurality of elements, on the detection surface, the plurality of elements being configured to convert an acoustic wave generated from an object irradiated with light into respective analog time-series signals and output the respective analog time-series signals;
    signal acquisition circuitry configured to convert the respective analog time-series signals into respective digital signals;
    a signal processing unit configured to:
        receive the digital signals;
        determine, from the received digital signals, an unwanted digital signal corresponding to an analog time-series signal having a signal portion whose waveform is reversed relative to a waveform of another signal portion in the analog time-series signal corresponding to the acoustic wave generated from the object, wherein said unwanted digital signal corresponds to at least one detecting element which is not in acoustic contact with the object;
        generate corrected digital signals by reducing, from the received digital signals, the determined unwanted digital signal; and
        generate object information using the corrected digital signals; and
    an image processor which forms image data of the object from the object information.

9. The object information acquiring apparatus according to claim 8, further comprising a memory unit which stores a predetermined template signal having a signal portion whose waveform is reversed relative to a waveform of another signal portion in the predetermined template signal,
    wherein the unwanted digital signal is a digital signal, from among the received digital signals, whose correlation value with the predetermined template signal is equal to or greater than a threshold value.

10. The object information acquiring apparatus according to claim 9, wherein said signal processing unit is configured to adjust the threshold value.

11. The object information acquiring apparatus according to claim 9, further comprising a holding unit configured to hold the object,
    wherein said memory unit stores the predetermined template signal created from a detection signal generated corresponding to an acoustic wave reflected by said holding unit.

12. The object information acquiring apparatus according to claim 8, further comprising a holding unit configured to hold the object.

13. An object information acquiring apparatus for an object not in complete acoustic contact with a detection surface, comprising:
- a holding unit configured to hold the object;
- a plurality of elements, on the detection surface, the plurality of elements being configured to convert an acoustic wave, generated from an object irradiated with light, into respective analog time-series signals and output the respective analog time-series signals;
- signal acquisition circuitry configured to convert the respective analog time-series signals into respective digital signals;
- a signal processing unit configured to:
  - receive the digital signals;
  - determine, from the received digital signals, an unwanted digital signal corresponding to an analog time-series signal having a signal portion whose waveform is reversed relative to a waveform of another signal portion in the analog time-series signal corresponding to the acoustic wave generated from the object, wherein said unwanted digital signal corresponds to at least one detecting element which is not in acoustic contact with the object;
  - generate corrected digital signals by reducing, from among the received digital signals outputted at a timing determined based on a thickness of the holding unit and sound velocity in the holding unit, the determined unwanted time-series signal; and
  - generate object information using the corrected digital signals; and
- an image processor which forms image data of the object from the object information.

14. The object information acquiring apparatus according to claim 13, further comprising a memory unit which stores a predetermined template signal having a signal portion whose waveform is reversed relative to a waveform of another signal portion in the predetermined template signal,
  wherein the determined unwanted time-series signals is a digital signal, from among the received digital signals, whose correlation value with the predetermined template signal is equal to or greater than a threshold value.

15. The object information acquiring apparatus according to claim 14, wherein said signal processing unit is configured to adjust the threshold value.

16. The object information acquiring apparatus according to claim 14, wherein said memory unit stores the predetermined template signal created from a detection signal generated corresponding to an acoustic wave reflected by said holding unit.

* * * * *